(12) United States Patent
Ayers

(10) Patent No.: US 7,883,742 B2
(45) Date of Patent: Feb. 8, 2011

(54) POROUS MATERIALS DERIVED FROM POLYMER COMPOSITES

(75) Inventor: Michael Raymond Ayers, Palm Coast, FL (US)

(73) Assignee: Roskilde Semiconductor LLC, Las Vegas, NV (US)

( * ) Notice: Subject to any disclaimer, the term of this patent is extended or adjusted under 35 U.S.C. 154(b) by 600 days.

(21) Appl. No.: 11/806,463

(22) Filed: May 31, 2007

(65) Prior Publication Data

US 2007/0292700 A1    Dec. 20, 2007

Related U.S. Application Data

(60) Provisional application No. 60/809,402, filed on May 31, 2006.

(51) Int. Cl.
*B05D 3/00* (2006.01)

(52) U.S. Cl. .................. 427/243; 427/352; 427/384; 427/385.5; 427/240; 427/421.1; 427/430.1

(58) Field of Classification Search .............. None
See application file for complete search history.

(56) References Cited

U.S. PATENT DOCUMENTS

| | | | |
|---|---|---|---|
| 4,002,800 A | 1/1977 | Nestler et al. |
| 4,652,467 A | 3/1987 | Brinker et al. |
| 4,987,101 A | 1/1991 | Kaanta et al. |
| 5,103,288 A | 4/1992 | Sakamoto et al. |
| 5,145,546 A | 9/1992 | Yuasa et al. |
| 5,177,248 A | 1/1993 | Chiang et al. |
| 5,294,732 A | 3/1994 | Chiang et al. |
| 5,308,481 A | 5/1994 | Stalling et al. |
| 5,338,571 A | 8/1994 | Mirkin et al. |
| 5,364,993 A | 11/1994 | Zhang et al. |
| 5,386,048 A | 1/1995 | West et al. |
| 5,416,188 A | 5/1995 | Chiang et al. |
| 5,420,081 A | 5/1995 | Mattes et al. |
| 5,470,820 A | 11/1995 | Hauser et al. |
| 5,494,859 A | 2/1996 | Kapoor |
| 5,679,861 A | 10/1997 | Kuo et al. |
| 5,698,140 A | 12/1997 | Lamb et al. |
| 5,739,376 A | 4/1998 | Bingel |
| 5,744,399 A | 4/1998 | Rostoker et al. |
| 5,801,092 A | 9/1998 | Ayers |
| 5,851,503 A | 12/1998 | Mitani et al. |

(Continued)

FOREIGN PATENT DOCUMENTS

EP    0 647 606 A1    4/1995

(Continued)

OTHER PUBLICATIONS

Bell et al, Proceedings—Electrochemcial Society (1994), 92-94, pp. 92-106.*

(Continued)

*Primary Examiner*—Erma Cameron
(74) *Attorney, Agent, or Firm*—Sterne Kessler Goldstein & Fox (57) ABSTRACT

This disclosure relates generally to networks of polymers in fullerene compounds and polymers, to methods of preparing precursors for such networks, and to their subsequent use as low dielectric constant materials in microelectronic devices.

15 Claims, 4 Drawing Sheets

U.S. PATENT DOCUMENTS

| | | | |
|---|---|---|---|
| 5,965,202 A | 10/1999 | Taylor-Smith et al. | |
| 6,066,272 A | 5/2000 | Tang et al. | |
| 6,083,624 A | 7/2000 | Hiura | |
| 6,113,673 A | 9/2000 | Loutfy et al. | |
| 6,187,427 B1 | 2/2001 | Taylor-Smith et al. | |
| 6,214,746 B1 | 4/2001 | Leung et al. | |
| 6,255,241 B1 | 7/2001 | Miyazawa et al. | |
| 6,277,766 B1 | 8/2001 | Ayers | |
| 6,287,979 B1 | 9/2001 | Zhou et al. | |
| 6,342,454 B1 * | 1/2002 | Hawker et al. | 438/780 |
| 6,368,569 B1 | 4/2002 | Haddon et al. | |
| 6,380,270 B1 | 4/2002 | Yates | |
| 6,423,811 B1 | 7/2002 | Lau et al. | |
| 6,495,479 B1 * | 12/2002 | Wu et al. | 438/781 |
| 6,599,492 B2 | 7/2003 | Iwamura et al. | |
| 6,621,970 B2 | 9/2003 | Khudyakov et al. | |
| 6,713,590 B2 | 3/2004 | Lau et al. | |
| 6,743,481 B2 | 6/2004 | Hoehn et al. | |
| 6,790,790 B1 | 9/2004 | Lyons et al. | |
| 6,797,777 B2 | 9/2004 | Lau et al. | |
| 6,855,202 B2 | 2/2005 | Alivisatos et al. | |
| 6,967,222 B2 | 11/2005 | Khanarian et al. | |
| 6,984,265 B1 | 1/2006 | Raguse et al. | |
| 6,987,147 B2 | 1/2006 | Lau et al. | |
| 6,998,178 B2 | 2/2006 | Apen et al. | |
| 7,011,890 B2 | 3/2006 | Nguyen et al. | |
| 7,014,681 B2 | 3/2006 | Noack et al. | |
| 7,060,204 B2 | 6/2006 | Li et al. | |
| 7,338,812 B2 | 3/2008 | Lin et al. | |
| 7,531,209 B2 * | 5/2009 | Ayers | 427/230 |
| 2001/0016608 A1 | 8/2001 | Haddon et al. | |
| 2001/0041801 A1 | 11/2001 | Friedman et al. | |
| 2002/0016414 A1 | 2/2002 | Lau et al. | |
| 2002/0037941 A1 | 3/2002 | Lau et al. | |
| 2002/0061397 A1 | 5/2002 | Iwamura et al. | |
| 2003/0072947 A1 | 4/2003 | Lee et al. | |
| 2003/0151031 A1 | 8/2003 | Li et al. | |
| 2003/0162002 A1 | 8/2003 | Lau et al. | |
| 2003/0187139 A1 | 10/2003 | Lau et al. | |
| 2003/0213958 A1 | 11/2003 | Nakagawa et al. | |
| 2004/0005506 A1 | 1/2004 | Nishimura | |
| 2004/0038408 A1 | 2/2004 | Abbott et al. | |
| 2004/0046155 A1 | 3/2004 | Li et al. | |
| 2004/0102584 A1 | 5/2004 | Lau et al. | |
| 2004/0121501 A1 * | 6/2004 | Large et al. | 438/40 |
| 2004/0132846 A1 | 7/2004 | Leventis et al. | |
| 2004/0175568 A1 | 9/2004 | Takaguchi | |
| 2004/0175581 A1 | 9/2004 | Nguyen et al. | |
| 2004/0180201 A1 | 9/2004 | Veedu et al. | |
| 2004/0185448 A1 | 9/2004 | Lopez-Avila | |
| 2004/0250750 A1 | 12/2004 | Reda et al. | |
| 2005/0020702 A1 | 1/2005 | Li et al. | |
| 2005/0089684 A1 | 4/2005 | Barron et al. | |
| 2005/0119360 A1 | 6/2005 | Kawakami et al. | |
| 2005/0238889 A1 | 10/2005 | Iwamoto et al. | |
| 2005/0263908 A1 | 12/2005 | Nakagawa et al. | |
| 2005/0279399 A1 | 12/2005 | Gaudiana et al. | |
| 2006/0002875 A1 | 1/2006 | Winkler et al. | |
| 2006/0024502 A1 | 2/2006 | McFarland et al. | |
| 2006/0071300 A1 | 4/2006 | Haverty et al. | |
| 2006/0093885 A1 | 5/2006 | Krusic et al. | |
| 2006/0106152 A1 | 5/2006 | Metzinger et al. | |
| 2006/0155376 A1 | 7/2006 | Asgari | |
| 2006/0175685 A1 * | 8/2006 | Shin et al. | 257/632 |
| 2006/0185794 A1 | 8/2006 | Ayers | |
| 2009/0192281 A1 | 7/2009 | Ayers | |

FOREIGN PATENT DOCUMENTS

| | | |
|---|---|---|
| EP | 1 015 384 B1 | 7/2000 |
| EP | 1 063 197 A2 | 12/2000 |
| EP | 1 190 422 B1 | 3/2002 |
| EP | 1 244 731 B1 | 10/2002 |
| EP | 1 265 080 A2 | 12/2002 |
| EP | 1 473 770 A1 | 11/2004 |
| GB | 2 380 496 A | 4/2003 |
| JP | 5-254955 A | 10/1993 |
| JP | 6-324681 A | 11/1994 |
| JP | 8-181133 A | 7/1996 |
| JP | 8-245209 A | 9/1996 |
| JP | 9-316202 A | 12/1997 |
| JP | 10-310709 A | 11/1998 |
| JP | 11-263916 A | 9/1999 |
| JP | 2000-154191 A | 6/2000 |
| JP | 2000-268632 A | 9/2000 |
| JP | 2001-192322 A | 7/2001 |
| JP | 2002-6478 A | 1/2002 |
| JP | 2002-72964 A | 3/2002 |
| JP | 2003-3047 A | 1/2003 |
| JP | 2003-3119 A | 1/2003 |
| JP | 2003-176113 A | 6/2003 |
| JP | 2003-280249 A | 10/2003 |
| JP | 2003-321214 A | 11/2003 |
| JP | 2004-182771 A | 7/2004 |
| JP | 2005-53832 A | 3/2005 |
| JP | 2005-105152 A | 4/2005 |
| JP | 2005-119167 A | 5/2005 |
| JP | 2005-144601 A | 6/2005 |
| JP | 2005-263509 A | 9/2005 |
| JP | 2005-268550 A | 9/2005 |
| JP | 2005-272639 A | 10/2005 |
| JP | 2005-289755 A | 10/2005 |
| JP | 2005-290316 A | 10/2005 |
| WO | WO 98/07793 A1 | 2/1998 |
| WO | WO 00/68956 A1 | 11/2000 |
| WO | WO 01/25316 A1 | 4/2001 |
| WO | WO 01/78110 A2 | 10/2001 |
| WO | WO 01/91922 A2 | 12/2001 |
| WO | WO 02/06366 A1 | 1/2002 |
| WO | WO 02/30814 A1 | 4/2002 |
| WO | WO 02/081546 A1 | 10/2002 |
| WO | WO 03/018645 A1 | 3/2003 |
| WO | WO 03/057749 A1 | 7/2003 |
| WO | WO 03/060979 A2 | 7/2003 |
| WO | WO 03/061029 A2 | 7/2003 |
| WO | WO 2004/000909 A1 | 12/2003 |
| WO | WO 2004/079814 A2 | 9/2004 |
| WO | WO 2005/008761 A1 | 1/2005 |
| WO | WO 2005/010071 A1 | 2/2005 |
| WO | WO 2005/028174 A2 | 3/2005 |
| WO | WO 2006/023921 A2 | 3/2006 |
| WO | WO 2006/028704 A2 | 3/2006 |
| WO | WO 2006/028776 A1 | 3/2006 |

OTHER PUBLICATIONS

Chen, K., et al., "Fullerene Self-Assembly onto $(MeO)_3Si(CH_2)_3NH_2$-Modified Oxide Surfaces," *J. Am. Chem. Soc.* 115:1193-1194, American Chemical Society (1993).

Hirsch, A., et al., "Globe-trotting Hydrogens on the Surface of the Fullerene Compound $C_{60}H_6(N(CH_2CH_2)_2O)_6$," *Angew. Chem. Int. Ed. Engl.* 30:1309-1310, VCH Verlagsgesellschaft mbH (1991).

Hirsch, A., et al., "Regioselective Multiple Additions to Buckminsterfullerene," in *The Chemical Physics of Fullerenes 10 (and 5) Years Later*, Andreoni, W., ed., Kluwer Academic Publishers, Boston, MA, pp. 267-283 (1996).

Jenekhe, S.A., and Chen, X.L., "Self-Assembly of Ordered Microporous Materials from Rod-Coil Block Copolymers," *Science* 283:372-375, American Association for the Advancement of Science (1999).

Liang, C., et al., "Synthesis of a Large-Scale Highly Ordered Porous Carbon Film by Self-Assembly of Block Copolymers," *Angew. Chem. Int. Ed.* 43:5785-5789, Wiley-VCH Verlag GmbH & Co. KGaA (Nov. 2004).

Maggini, M., et al., "$C_{60}$ Derivatives Embedded in Sol-Gel Silica Films," *Adv. Mater.* 7:404-406, VCH Verlagsgesellschaft mbH (1995).

Ouyang, J., et al., "Structures and Properties of Supramolecular Assembled Fullerenol/Poly(dimethylsiloxane) Nanocomposites," *J. Phys. Chem. B 108*:5937-5943, American Chemical Society (May 2004).

Wudl, F., et al., "Survey of Chemical Reactivity of $C_{60}$, Electrophile and Dieno-polarophile Par Excellence," in *ACS Symposium Series—Fullerenes*, Hammond, G.S., and Kuck, V.J., eds., American Chemical Society, Washington, DC, pp. 161-175 (1992).

Yevlampieva, N., et al., "Star-like Fullerene Containing Poly(Vinylpyrrolydone) Derivatives: Chloroform Solution Properties," *Fullerenes, Nanotubes, and Carbon Nanostructures 12*:353-359, Marcel Dekker, Inc. (Aug. 2004).

Patent Abstracts of Japan, unverified English language abstract for JP 5-254955 A (Document FP1 listed on accompanying PTO/SB/08A).

Patent Abstracts of Japan, unverified English language abstract for JP 6-324681 A (Document FP2 listed on accompanying PTO/SB/08A).

Patent Abstracts of Japan, unverified English language abstract for JP 8-181133 A (Document FP4 listed on accompanying PTO/SB/08A).

Patent Abstracts of Japan, unverified English language abstract for JP 8-245209 A (Document FP5 listed on accompanying PTO/SB/08A).

Patent Abstracts of Japan, unverified English language abstract for JP 9-316202 A (Document FP6 listed on accompanying PTO/SB/08A).

Patent Abstracts of Japan, unverified English language abstract for JP 11-0263916 A (Document FP7 listed on accompanying PTO/SB/08A).

Patent Abstracts of Japan, unverified English language abstract for JP 10-310709 A (Document FP8 listed on accompanying PTO/SB/08A).

Patent Abstracts of Japan, unverified English language abstract for JP 2000-154191 A (Document FP10 listed on accompanying PTO/SB/08A).

Patent Abstracts of Japan, unverified English language abstract for JP 2000-268632 A (Document FP11 listed on accompanying PTO/SB/08A).

Patent Abstracts of Japan, unverified English language abstract for JP 2001-192322 A (Document FP15 listed on accompanying PTO/SB/08A).

Patent Abstracts of Japan, unverified English language abstract for JP 2002-6478 A (Document FP18 listed on accompanying PTO/SB/08A).

Patent Abstracts of Japan, unverified English language abstract for JP 2002-72964 A (Document FP19 listed on accompanying PTO/SB/08A).

Patent Abstracts of Japan, unverified English language abstract for JP 2003-3047 A (Document FP26 listed on accompanying PTO/SB/08A).

Patent Abstracts of Japan, unverified English language abstract nslation for JP 2003-3119 A (Document FP27 listed on accompanying PTO/SB/08A).

Patent Abstracts of Japan, unverified English language abstract for JP 2003-176113 A (Document FP30 listed on accompanying PTO/SB/08A).

Patent Abstracts of Japan, unverified English language abstract for JP 2003-280249 A (Document FP34 listed on accompanying PTO/SB/08A).

Patent Abstracts of Japan, unverified English language abstract for JP 2003-321214 A (Document FP36 listed on accompanying PTO/SB/08A).

Patent Abstracts of Japan, unverified English language abstract for JP 2004-182771 A (Document FP37 listed on accompanying PTO/SB/08A).

Patent Abstracts of Japan, unverified English language abstract for JP 2005-53832 A (Document FP42 listed on accompanying PTO/SB/08A).

Patent Abstracts of Japan, unverified English language abstract for JP 2005-105152 A (Document FP44 listed on accompanying PTO/SB/08A).

Patent Abstracts of Japan, unverified English language abstract for JP 2005-119167 A (Document FP45 listed on accompanying PTO/SB/08A).

Patent Abstracts of Japan, unverified English language abstract for JP 2005-144601 A (Document FP46 listed on accompanying PTO/SB/08A).

Patent Abstracts of Japan, unverified English language abstract for JP 2005-263509 A (Document FP47 listed on accompanying PTO/SB/08A).

Patent Abstracts of Japan, unverified English language abstract for JP 2005-268550 A (Document FP48 listed on accompanying PTO/SB/08A).

Patent Abstracts of Japan, unverified English language abstract for JP 2005-272639 A (Document FP49 listed on accompanying PTO/SB/08A).

Patent Abstracts of Japan, unverified English language abstract for JP 2005-289755 A (Document FP50 listed on accompanying PTO/SB/08A).

Patent Abstracts of Japan, unverified English language abstract for JP 2005-290316 A (Document FP51 listed on accompanying PTO/SB/08A).

Dialog File 351, Accession No. 7111280, unverified English language abstract for EP 0 647 606 A1 (Document FP3 listed on accompanying PTO/SB/08A).

Jena, P., and Khanna, S.N., "Physics of cluster assembled materials," *Mater. Sci. Eng. A217/A218*:218-222, Elsevier Science S.A. (1996).

Matsuura, M., et al., "On the role of small additives for nanocrystalline formation from amorphous matrix," *Mater. Sci. Eng. A217/A218*:397-400, Elsevier Science S.A. (1996).

Ohno, K., et al., "Ab-initio molecular dynamics study of the stability and reactivity of $C_{60}$," *Mater. Sci. Eng. A217/A218*:19-22, Elsevier Science S.A. (1996).

Co-pending U.S. Appl. No. 11/806,464, inventor Ayers, M.R., filed May 31, 2007 (Not Published).

Co-pending U.S. Appl. No. 11/806,482, inventor Ayers, M.R., filed May 31, 2007 (Not Published).

Co-pending U.S. Appl. No. 11/806,465, inventor Ayers, M.R., filed May 31, 2007 (Not Published).

The International Search Report completed for Application No. PCT/US07/12836 on Sep. 20, 2007 and mailed on Nov. 5, 2007.

The International Search Report completed for Application No. PCT/US07/12835 on Oct. 3, 2007 and mailed on Nov. 28, 2007.

The International Search Report completed for Application No. PCT/US07/12831 on Oct. 19, 2007 and mailed on Dec. 5, 2007.

A Non-Final Office Action issued in the co-pending U.S. Appl. No. 10/906,534 on Nov. 27, 2007.

The International Search Report completed for Application No. PCT/US07/12832 on Oct. 24, 2007 and mailed on Dec. 18, 2007.

Non Final Office Action in U.S. Appln. No. 11/806,465, mailed Oct. 20, 2010, 6 pgs.

Non Final Office Action in U.S. Appln. No. 12/418,314, mailed Sep. 29, 2010, 7 pgs.

Xia et al., Proceedings of SPIE, 3136, 1997, pp. 57-61.

Ulug et al., Fullerene Science and Technology, 5(7), 1997, pp. 1651-1658.

Wang, Tetrahedron, 58, 2002, pp. 2377-2380.

Office Action from Examiner Fletcher in parent U.S. Appl. No. 10/906,534, mailed on Nov. 27, 2007.

Office Action from Examiner Fletcher in related parent U.S. Appl. No. 10/906,534, mailed on Jun. 30, 2008.

Non Final Office Action in U.S. Appln. No. 11/806,464, mailed Jan. 20, 2010, 6 pgs.

Final Office Action in U.S. Appln. No. 11/806,464, mailed May 14, 2010, 6 pgs.

Non Final Office Action in U.S. Appln. No. 11/806,465, mailed Apr. 6, 2010, 8 pgs.

Final Office Action in U.S. Appln. No. 11/806,465, mailed Jul. 14, 2010, 7 pgs.

Non Final Office Action in U.S. Appln. No. 11/806,482, mailed Jan. 27, 2010, 6 pgs.

* cited by examiner

POROUS MATERIALS DERIVED FROM POLYMER COMPOSITES

CROSS REFERENCE TO RELATED APPLICATIONS

This application is claims the benefit of U.S. Provisional Patent Application No. 60/809,402, filed May 31, 2006, the disclosure of which is incorporated by reference herein in its entirety.

BACKGROUND OF THE INVENTION

Field of the Invention

This disclosure relates generally to fullerene-comprising compounds, methods of preparing such compounds, and to their subsequent use as low dielectric constant materials in microelectronic devices.

BRIEF SUMMARY OF THE INVENTION

In one embodiment, the present invention provides methods of producing a porous film. In suitable embodiments, a polyfunctional fullerene monomer comprising at least one reactive arm is provided. A composite precursor solution comprising the polyfunctional fullerene monomer and at least one organic polymer porogen is then prepared. The composite is then applied to a substrate and the polyfunctional monomer cured. At least a portion of the porogen is then removed to form the porous film. In exemplary embodiments, the polyfunctional fullerene monomer comprises a fullerene (e.g., $C_{60}$) and at least one reactive arm comprising: a reactive group coupled to the fullerene; an organic spacer portion; and a metal or metalloid alkoxide. Exemplary reactive arms suitably comprise: an amine, an azide, a diene or a carbanion; an alkyl organic spacer portion; and a metal or metalloid alkoxide selected from the group consisting of —$Si(OR)_3$, —$Ge(OR)_3$, —$Ti(OR)_3$, —$Zr(OR)_3$, —$Sn(OR)_3$, —$Al(OR)_2$ and —$B(OR)_2$. For example, the reactive arms can be 3-aminopropyltrimethoxysilane, 3-aminopropyltriethoxysilane, 2-aminoethyl-3-aminopropyltrimethoxysilane, 2-aminoethyl-3-aminopropyltriethoxysilane, diethylenetriaminopropyltrimethoxysilane, hexane-diaminomethyltriethoxysilane or 11-aminoundecyltriethoxysilane.

Exemplary porogens for use in the practice of the present invention include acrylate-based polymers such as poly(methyl methacrylate). Suitably methods for applying the composite include, spin-coating, dip-coating or spray-coating. Suitably, the curing comprises heating to between about 50° C. to 120° C. in a moist atmosphere. In some embodiments, the curing comprises heating the functionalized fullerenes to greater than about 80° C. Exemplary methods for removing the porogen include thermal baking, for example, heating to between about 150° C. to 350° C. in an inert atmosphere. In some embodiments, the removing comprises heating the functionalized fullerenes to greater than about 200° C. in an inert atmosphere.

The present invention also provides methods of producing a porous film. For example, a plurality of $C_{60}$ fullerenes are provided, and then aminohexyltriethoxysilane is added to the fullerenes, wherein amino groups of the aminohexyltriethoxysilane react with the fullerenes to generate functionalized fullerenes. The functionalized fullerenes are combined with poly(methyl methacrylate) to generate a composite and then applied the to a substrate. The polyfunctional monomer is then cured, and at least a portion of the poly(methyl methacrylate) is removed to form a porous film. In further embodiments, films, including films produced by the methods of the present invention, are provided.

DETAILED DESCRIPTION OF THE INVENTION

The derivatized fullerene monomers of the present disclosure, used as precursors to matrix-forming polymers, and which are well-suited for forming highly crosslinked three-dimensional networks, include a central core comprising a fullerene that is subsequently derivatized by a plurality of radial arms. Such derivatized fullerene molecules possess a high solubility in common solvents and the ability to form three-dimensional network polymers upon condensation with adjacent clusters. The clusters and polymers prepared according to the present disclosure are largely composed of fragments exhibiting intrinsically low dielectric constants.

The present invention also relates to methods for combining the monomers with a thermally labile organic polymer porogen to form a composite structure, depositing the composite structure as a film on a desired substrate, polymerizing the fullerene-containing matrix material, and subsequently removing the polymer porogen to yield a porous polymer film, especially when such films are used as intra- or interlayer dielectrics for microelectronic devices. Any preparative route that produces a similar soluble, reactive fullerene monomer, where the core is symmetrically surrounded by one or more arms each terminated by a reactive group may be used. One method involves the use of a bifunctional coupling agent to form the arms that contain, at one end an amine group and at the opposite end a metal- or metalloid-alkoxide. Any coupling agent which is capable of both reacting with a fullerene and undergoing condensation reactions with other identical coupling agents may be used.

The fullerene core of the organic phase precursor monomers includes, but is not limited to one or more of the following: $C_{60}$, $C_{70}$, $C_{72}$, $C_{74}$, $C_{76}$, $C_{78}$, $C_{84}$, $C_{96}$, and higher analogues up to, and beyond, $C_{184}$ or mixtures thereof. Commercially available mixtures of $C_{60}$ and $C_{70}$, commonly know as Fullerite, fullerene extract, or fullerene soot may also be employed in various embodiments of the present invention.

Many possible compounds that are well-suited to form the reactive arms of the organic phase precursor monomers are readily available. The reactive arms include three general parts; a terminal group known to react with fullerenes, a linear organic spacer, and an opposing terminal group capable of undergoing multiple condensation reactions, or which is cross-linkable, with similar groups.

Any terminal group capable of forming covalent bonds with the fullerene core may be used. For example, terminal groups to couple the arms to the fullerene core include a primary or secondary amine. Amines are known to those skilled in the art to react with fullerenes in a facile manner by nucleophilic addition reactions across one of the many delocalized bonds of the fullerene cage. Anywhere from one to twelve amine molecules may be added to a single $C_{60}$ molecule, the actual number depending largely on their steric bulk. One example being six. Other reactive groups, especially other nucleophiles, may be used, which include, but are not limited to azides, dienes, and carbanions.

The organic-spacer portion of the coupling agent may be any spacer group capable of connecting the terminal groups. For example, the spacer groups include, but are not limited to an alkyl chain, a polyether chain, a polyunsaturated alkyl chain, or an amine-containing alkyl chain. In one example, the organic spacer is an alkyl chain 3-20 carbon units long, alternatively 3-7 carbon units long. The spacer chain may include one or more heteroatomic groups, such as ether groups or amino groups, and optionally, may further include one or more rigid components, including, but not limited to alkynyl-segments, aryl-segments, or other cyclic segments.

The opposing terminal reactive group used for linking the organic phase monomers to each other and to the other components of the composite structure may be any cross-linkable group. For example, the cross-linkable terminal group includes, but is not limited to, metal- or metalloid-alkoxides. Alkoxides are well known in the art to readily undergo hydrolysis and condensation reactions, forming polymeric oxides, and to bond with, upon hydrolysis, the chemically similar surfaces of solid oxides. Any one of numerous possible alkoxide groups may be used according to the present disclosure, including, but not limited to, $-Si(OR)_3$, $-Ge(OR)_3$—$Ti(OR)_3$, $-Zr(OR)_3$, $-Sn(OR)_3$, $-Al(OR)_2$, $-B(OR)_2$. In one embodiment, as silica is a well known dielectric material, an example of a terminal group is $-Si(OR)_3$.

The following are non-limiting examples of commercially available coupling agents which can be used in the practice of the present invention; 3-aminopropyltrimethoxysilane, 3-aminopropyltriethoxysilane, 2-aminoethyl-3-aminopropyltrimethoxysilane, 2-aminoethyl-3-aminopropyltriethoxysilane, diethylenetriamino-propyltrimethoxysilane, hexanediaminomethyltriethoxysilane, 11-aminoundecyltriethoxysilane. However, numerous additional compounds may prove useful.

Figure 1:
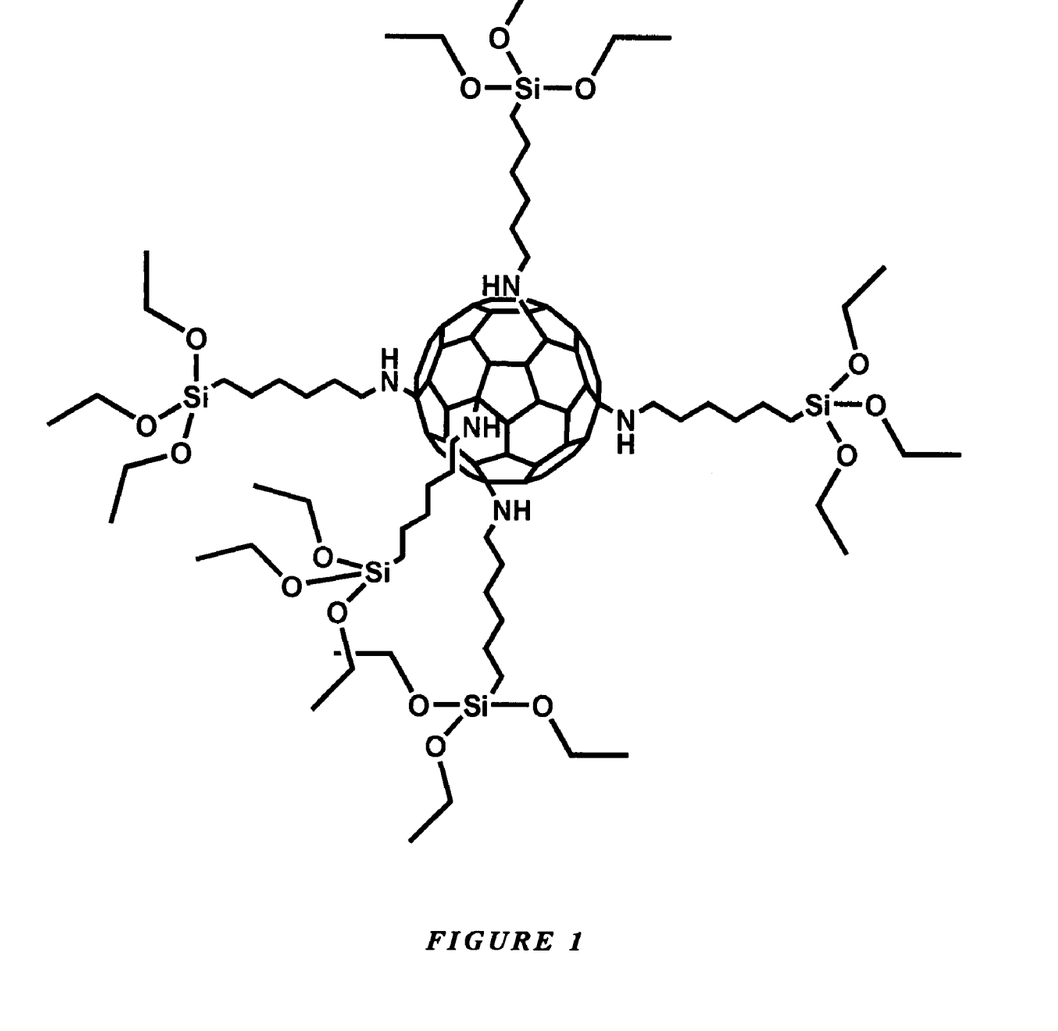
FIG. 1 shows a typical polyfunctional fullerene monomer.

The preparation of the polyfunctional fullerene monomer may be readily achieved. The desired amount of the selected fullerene core is added to a large excess of the selected coupling agent. Initially, the fullerene is insoluble in the coupling agent and is present as a fine black suspension. Reaction of the amine group of the coupling agent with the fullerene occurs readily at ambient temperature. However, heating the mixture to 50-60° C. allows the reaction to proceed at a more desirable rate. As the reaction proceeds, the partially derivatized fullerenes exhibit increased solubility in the coupling agent and the mixture exists as a dark brown solution. After approximately 18 hours, the formation of the organic phase precursor monomer is complete, with the maximum number of coupling agents, typically six, being added to the fullerene core. The unreacted coupling agent is removed using vacuum-distillation and recovered for use in future preparations, leaving a deep brown-black residue containing the organic phase precursor monomer. An example of such a compound, derived from $C_{60}$ and 6-aminohexyltriethoxysilane is shown in FIG. 1.

The derivatized fullerene monomers possesses a high solubility in many common organic solvents, including alkanes, toluene, benzene, ketones, and alcohols. Examples of alcohols for use in the present invention include, but are not limited to ethanol and 2-propanol, which are solvents employed for the deposition of spin-on inorganic films in the microelectronics industry. The residue prepared as above may be redissolved in a solvent suitable for application to the desired substrate, such as ethanol.

The fullerene monomers may form network polymers though condensation reactions with adjacent monomers or clusters of monomers. With multiple reactive arms surrounding each monomer fullerene core, each monomer can form several strong links with neighboring monomers. Highly-crosslinked polymers show significant increases in both thermal stability and mechanical strength relative to similar polymers that are less crosslinked. Both of these qualities are important for a material that is intended for use in microelectronic devices, where temperatures of 400° C. as well as strong mechanical forces are common during processing.

The polyfunctional fullerene monomers may also form strong bonds to common substrates encountered in microelectronic structures. These substrates include, but are not limited to oxides and metals, two classes of materials that form strong bonds to films containing alkoxides. Excellent film adhesion is a property that a successful dielectric material should possess to achieve use in practice. With multiple reactive groups per cluster, the fullerene monomer may form strong bonds to a desired substrate, especially relative to other organic polymers found in the art.

The matrix-forming polyfunctional fullerene monomer may be combined with an organic polymeric porogen material in a suitable solvent, to form a precursor solution for the composite structure used to form the final porous film. The material for the porogen phase is suitably thermally or chemically removable under conditions that do not degrade the fullerene-containing matrix. In addition, the material suitably will be adequately soluble in a solvent, or mixture of solvents that also show good solvating ability towards the matrix-forming fullerene monomers. The porogen is suitably miscible with the matrix-forming monomer in proportions adequate to yield the desired amount of final film porosity, and it should be available in a suitable range of molecular weights to form pores of the desired size.

Examples of porogens for use in the present invention include acrylate-based polymer porogens. One example of a porogen for use includes, but is not limited to, poly(methyl methacrylate). This polymer is widely available in various desirable molecular weights, shows good solubility in useful solvents such as ketones and ethers, and is easily thermally depolymerized with the onset occurring above 150° C. These may be derived from copolymers of methyl methacrylate with other acrylate esters, from direct polymerization of other acrylate monomers, or from copolymers with other monomers such as styrene. Currently available examples of other useful acrylate-based polymer porogens include, but are not limited to, poly(methyl methacrylate-co-ethyl acrylate), poly(methyl methacrylate-co-ethylene glycol dimethacrylate), poly(methyl methacrylate-co-butyl methacrylate), poly(styrene-co-methyl methacrylate), or poly(styrene-co-butadiene-co-methyl methacrylate). Alternatively, the polymeric porogen may include either a linear polymer or a crosslinked polymer formed by any common crosslinking agent including, but not limited to, allylmethacrylate or 1,3,5-trivynylbenzene.

The ratio of the matrix-forming monomer and the porogen is chosen such that each phase exists as a continuous network conterminous with the other phase. This is provides a free path for the subsequent removal of the porogen, to avoid the formation of pores larger than about 20 nm in diameter, and to leave a strong, continuous matrix after the porogen has been removed. Additionally, the amount of porogen is suitably sufficient to ensure that the desired level of porosity of the final film is achieved, with a corresponding lowering of the film's dielectric constant. In one example, the porogen occupies between about 30% and 60% of the volume of the dried composite film after deposition onto the desired substrate. Other compositions that yield a suitably strong porous film may also be used.

Figure 2:
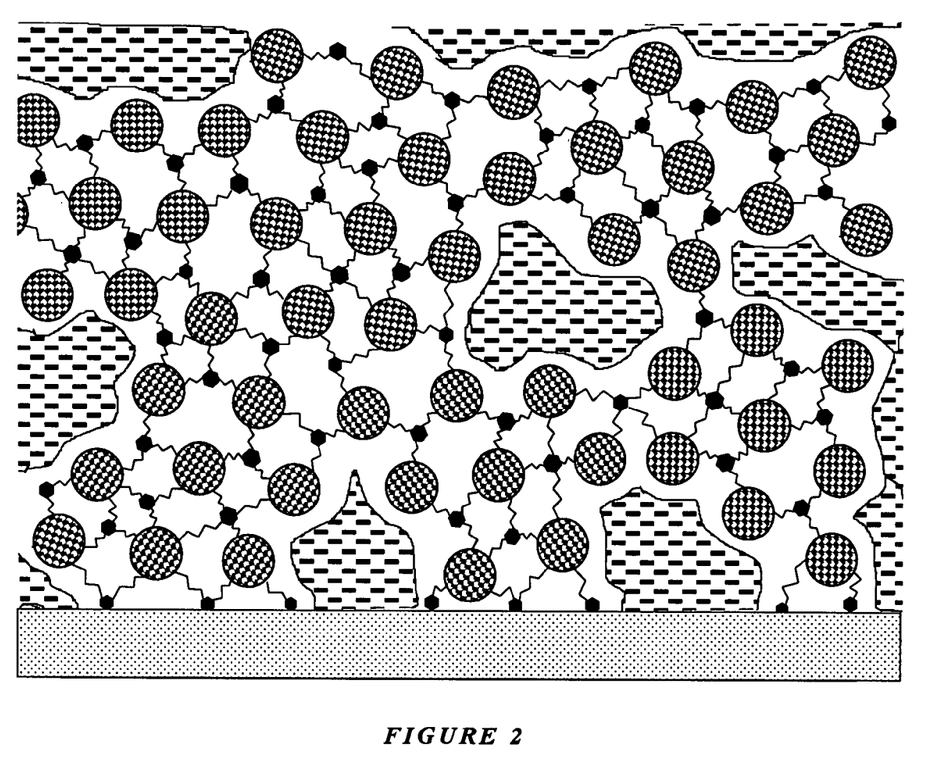
FIG. 2 shows a representation of a section of the composite structure of the fullerene cluster polymer and polymer porogen after deposition onto a substrate and initial curing. Fullerene cages are shown as hashed circles, junctions formed by the condensation of terminal groups of the radial arms are shown as black hexagons, the porogen is shown as a dashed solid, and the solid substrate is dotted.

A solution of the matrix-forming fullerene monomer may be combined with a solution of the chosen porogen, forming a composite film precursor solution. This solution is applied to the desired substrate by any method commonly employed in the art, such as spin-coating, dip-coating, or spray-coating. A subsequent initial thermo-chemical curing step removes residual solvent and initiates the hydrolysis and condensation reactions of the terminal alkoxide groups of the radial arms in the matrix-forming phase, crosslinking fullerene-containing monomers and bonding the entire composite structure to the solid substrate. This step is performed at a temperature and under an atmosphere sufficient to hydrolyze and condense the alkoxide groups of the matrix-forming monomers, but which will leave the porogen phase unaffected. The initial curing step is suitably performed between about 50° C. and about 120° C. under an atmosphere of moist air. A section of such a composite structure on a solid substrate is shown in FIG. 2. Fullerene cages are shown as hashed circles, junctions formed by the condensation of terminal groups of the radial arms are shown as black hexagons, the porogen is shown as a dashed solid, and the solid substrate is dotted.

Figure 3:
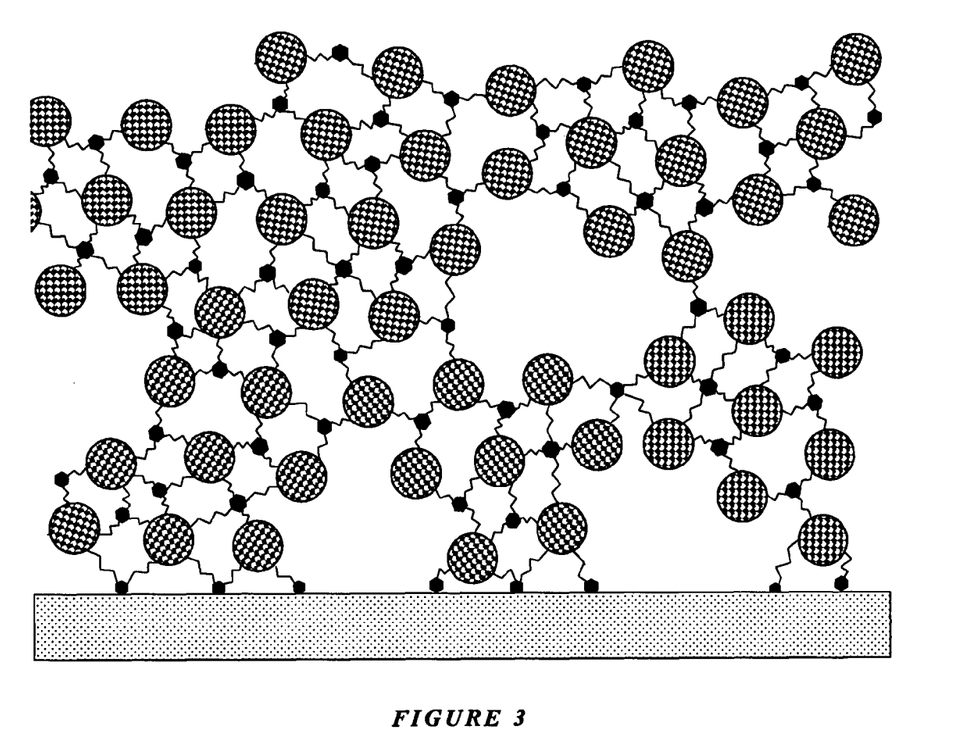
FIG. 3 shows the section of FIG. 2, after removal of the polymeric porogen.

The porogen phase may be removed during a subsequent thermal bake. This step is generally performed at a temperature, and under an atmosphere, which will depolymerize and volatilize the porogen, but leave the polymerized fullerene matrix unaffected. This typically requires an inert atmosphere, typically oxygen-free argon or nitrogen, and at temperatures in the range between about 150 and about 350° C., though temperatures outside of this range may be employed without departing from the methods of the present disclosure. FIG. 3 shows a representation of such a porous film after removal of the porogen. The film includes fullerenes (hashed circles) linked in a three-dimensional network by the condensation of the terminal groups of the reactive arms (black hexagons).

Alternatively, a portion or all of the porogen phase may be extracted from the composite film prior to the thermal cure. This is typically accomplished by contacting the film with a solvent capable of dissolving the porogen while leaving the fullerene polymer matrix unaffected.

The matrix materials of the films prepared as disclosed above possess both an intrinsically low dielectric constant, due to the low silica content of the fullerene polymer, and a controllable amount of porosity. The low dielectric constant of the fullerene polymer allows for a lower amount of porosity to be used when a certain dielectric constant is desired, relative to commonly used porous matrices with higher dielectric constants, such as silica.

Figure 4:
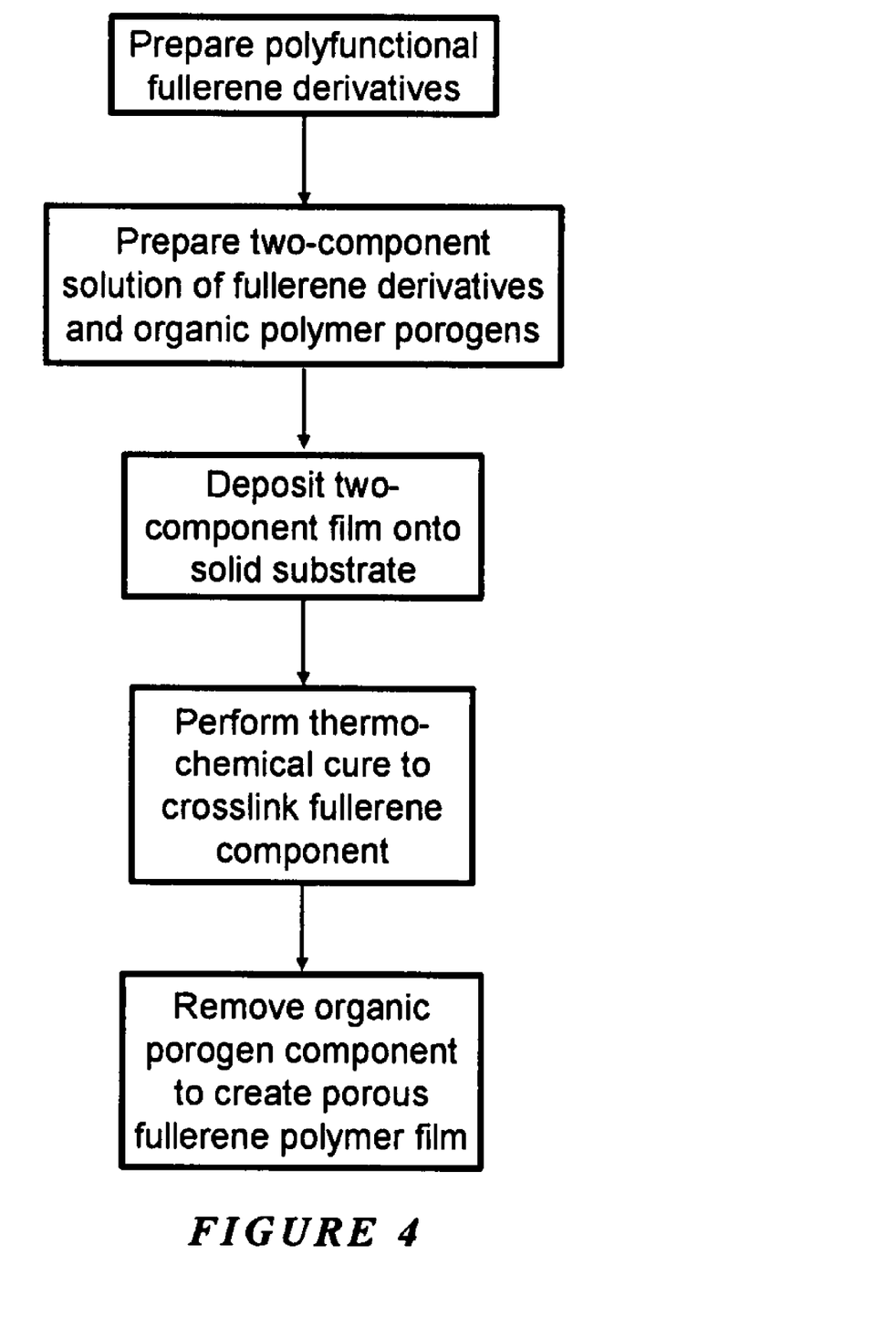
FIG. 4 shows a representation of the process steps disclosed herein.

A summary of the process steps typically contemplated according to the present disclosure is shown in FIG. 4.

EXAMPLES

The following non-limiting example demonstrates the experimental conditions suitable to prepare a microporous films of polymerized fullerene monomers, useful as low dielectric constant materials, according to the methods described hereinabove.

A porous, three-dimensional polymeric network of linked fullerenes with a low dielectric constant was prepared according to the processes of the present disclosure. A solution of a polyfunctional starburst-shaped fullerene molecule to be used as a monomer for said polymer was prepared as follows. About 0.50 grams of $C_{60}$ was mixed with about 20 mL of 6-aminohexyltriethoxysilane in a 100-mL Schlenk flask. The flask was flushed with dry nitrogen, and the mixture heated to about 60° C. for about 24 hours. During that time the mixture slowly changed from a clear liquid containing a fine black suspended powder to a dark brown solution with a moderate amount of a thick brown precipitate. The remaining 6-aminohexyltriethoxysilane was removed by vacuum distillation. This should be accomplished at the lowest possible pressure so that lower distillation temperatures may be employed. After the brown-black residue was dry, about a 0.250-gram portion was removed and dissolved in about 10 mL of anhydrous ethanol/10 mL of acetone. This solution was filtered to remove any undissolved material and reserved for use in the next step.

The above solution was mixed with a second solution of about 0.150 grams of poly(methylmethacrylate) (MW is about 50,000 g/mol) in methylisobutyl ketone. The composite precursor solution was coated onto a 2×2-cm section of silicon wafer and allowed to air dry. The coated substrate was then heated to about 60° C. for about 30 minutes to remove residual solvent. The temperature was then increased to about 90° C. and the substrate was held at that temperature under an atmosphere of moist air for about 120 minutes. The atmosphere was then exchanged for dry argon, and the temperature above the coated substrate was increased at a rate of about 5° C./min to about 200° C. and held at that temperature for about 60 minutes. A continued increase at about 5° C./min to about 350° C. and an isothermal bake at that temperature for about 30 minutes completed the removal of the porogen and the curing process. The resulting brown film contained approximately 50% porosity and exhibited excellent adhesion and scratch resistance and is well-suited for use as a low dielectric constant material.

Exemplary embodiments of the present invention have been presented. The invention is not limited to these examples. These examples are presented herein for purposes of illustration, and not limitation. Alternatives (including equivalents, extensions, variations, deviations, etc., of those described herein) will be apparent to persons skilled in the relevant art(s) based on the teachings contained herein. Such alternatives fall within the scope and spirit of the invention.

What is claimed is:

1. A method of producing a porous film, comprising:
   providing a functionalized fullerene monomer comprising at least one reactive arm;
   preparing a composite precursor solution comprising the functionalized fullerene monomer and at least one organic polymer porogen;
   applying the composite precursor solution to a substrate;
   curing the functionalized fullerene monomer; and
   removing at least a portion of the at least one organic polymer porogen to form a porous film having a three-dimensional network consisting of functionalized fullerenes.

2. The method of claim 1, wherein the functionalized fullerene monomer comprises a fullerene having at least one reactive arm, wherein the at least one reactive arm comprises:

a reactive group coupled to the fullerene; an organic spacer portion; and a metal or metalloid alkoxide.

3. The method of claim 2, wherein the functionalized fullerene monomer comprises a $C_{60}$ fullerene.

4. The method of claim 2, wherein the at least one reactive arm comprises: an amine, an azide, a diene or a carbanion; an alkyl organic spacer portion; and a metal or metalloid alkoxide selected from the group consisting of: —Si(OR)$_3$, —Ge(OR)$_3$, —Ti(OR)$_3$, —Zr(OR)$_3$, —Sn(OR)$_3$, —Al(OR)$_2$, and —B(OR)$_2$.

5. The method of claim 2, wherein the at least one reactive arm is selected from the group consisting of 3-aminopropyltrimethoxysilane, 3-aminopropyltriethoxysilane, 2-aminoethyl-3-aminopropyltrimethoxysilane, 2-aminoethyl-3-aminopropyltriethoxysilane, diethylenetriaminopropyltrimethoxysilane, hexane-diaminomethyltriethoxysilane, and 11-aminoundecyltriethoxysilane.

6. The method of claim 1, wherein the composite precursor solution comprises the functionalized fullerene monomer and an acrylate-based polymer as the at least one organic polymer porogen.

7. The method of claim 6, wherein the composite precursor solution comprises the functionalized fullerene monomer and poly(methyl methacrylate) as the at least one organic polymer porogen.

8. The method of claim 1, wherein the applying comprises spin-coating, dip-coating or spray-coating the composite precursor solution.

9. The method of claim 1, wherein the curing comprises heating the functionalized fullerene monomer to between about 50° C. to 120° C. in a moist atmosphere.

10. The method of claim 1, wherein the removing comprises thermal baking, thereby removing at least a portion of the at least one organic polymer porogen.

11. The method of claim 10, wherein the removing comprises heating to between about 150° C. to 350° C. in an inert atmosphere, thereby removing at least a portion of the at least one organic polymer porogen.

12. A method of producing a porous film, comprising:
providing a plurality of fullerenes;
adding aminohexyltriethoxysilane to the fullerenes, wherein amino groups of the aminohexyltriethoxysilane react with the fullerenes to generate functionalized fullerenes;
combining the functionalized fullerenes with poly(methyl methacrylate) to generate a composite solution;
applying the composite solution to a substrate;
curing the functionalized fullerenes; and
removing at least a portion of the poly(methyl methacrylate) to form a porous film having a three-dimensional network consisting of functionalized fullerenes.

13. The method of claim 12, wherein the applying comprises coating the composite solution on a silicon wafer.

14. The method of claim 12, wherein the curing comprises heating the functionalized fullerenes to greater than about 80° C.

15. The method of claim 12, wherein the removing comprises heating the functionalized fullerenes to greater than about 200° C. in an inert atmosphere.

* * * * *

UNITED STATES PATENT AND TRADEMARK OFFICE
CERTIFICATE OF CORRECTION

PATENT NO. : 7,883,742 B2  Page 1 of 1
APPLICATION NO. : 11/806463
DATED : February 8, 2011
INVENTOR(S) : Ayers

It is certified that error appears in the above-identified patent and that said Letters Patent is hereby corrected as shown below:

Title page, item (56), under "Other Publications", in Column 2, Line 1, delete "Electrochemcial" and insert -- Electrochemical --.

Page 3, item (56), under "Other Publications", in Column 1, Lines 50-51, after "abstract" delete "nslation".

Column 7, line 12, in Claim 5, delete "of" and insert -- of: --.

Signed and Sealed this
Seventh Day of June, 2011

David J. Kappos
*Director of the United States Patent and Trademark Office*